United States Patent [19]

Sturm

[11] Patent Number: 4,823,008
[45] Date of Patent: Apr. 18, 1989

[54] APPARATUS AND METHODS EMPLOYING INFRARED ABSORPTION MEANS TO MEASURE THE MOISTURE CONTENT OF HEAVY GRADES OF PAPER

[75] Inventor: Steven P. Sturm, Columbus, Ohio

[73] Assignee: Process Automation Business, Inc., Columbus, Ohio

[21] Appl. No.: 116,987

[22] Filed: Nov. 5, 1987

[51] Int. Cl.$^4$ .......................................... G01N 21/35
[52] U.S. Cl. ...................................... 250/339; 250/341; 250/359.1
[58] Field of Search ............ 250/339, 341, 340, 359.1; 356/435

[56] References Cited

U.S. PATENT DOCUMENTS

| | | | |
|---|---|---|---|
| 3,405,268 | 10/1968 | Brunton | 250/339 |
| 3,551,678 | 12/1970 | Mitchell | 250/341 |
| 3,661,462 | 5/1972 | Natens | 356/51 |
| 3,793,524 | 2/1974 | Howarth | 250/339 |
| 3,851,175 | 11/1974 | Dahlin et al. | 250/339 |
| 4,027,161 | 5/1977 | Williams et al. | 250/339 |
| 4,052,615 | 10/1977 | Cho | 250/341 |
| 4,097,743 | 6/1978 | Carlson | 250/339 |
| 4,171,918 | 10/1979 | Mactaggart | 356/408 |
| 4,300,049 | 11/1981 | Sturm | 250/339 |
| 4,306,151 | 12/1981 | Chase | 250/341 |
| 4,345,150 | 8/1982 | Tamura et al. | 250/339 |
| 4,577,104 | 3/1986 | Sturm | 250/339 |

OTHER PUBLICATIONS

Ya. A. Vakulyuk and I. T. Prilipko, "Infrared Water--Content Meter for Paper", *Measurement Techniques*, vol. 19, No. 7 (Jul. 1976), pp. 1065-1066. Translation of *Izmeritel'naya Teknika* published by Plenum Publishing Corporation, New York, Dec. 1976.
R. Goldstein, "The Near Infrared Absorption of Liquid Water at Temperatures Between 27° and 209° C.", in *Quantitative Spectroscopic Studies on Water Vapor and Liquid Water*, Technical Report No. 43 of the California Institute of Technology (Oct. 1963), pp. 24-37.
R. Goldstein, L. D. Gray, "Approximate Spectral Emissivity Calculations for Water Vapor at Elevated Temperatures", in *Quantitative Spectroscopic Studies on Water Vapor and Liquid Water*, Technical Report, No. 43 of the California Institute of Technology (Oct. 1963), pp. 38-42.

Primary Examiner—Janice A. Howell
Assistant Examiner—Constantine Hannaher
Attorney, Agent, or Firm—Richard H. Berneike

[57] ABSTRACT

Apparatus and methods for use in measuring the moisture content of heavy-grade sheets of paper during their continuous manufacture. In one aspect, means employing infrared absorption techniques for determining the fiber weight per unit area of a sheet having a fiber weight of up to 1100 grams per square meter are provided. In another aspect, means employing infrared absorption techniques including the use of two moisture absorption bands and associated moisture reference bands for calculating the average temperature of the sheet are provided. The latter aspect may be used to produce an indication of moisture weight per unit area, wherein the indication is substantially independent on changes in the average temperature, and enables accurate measurement of the moisture weight per unit area of heavy grades of paper having moisture weights of up to 450 grams per square meter. The former aspect may be employed in measuring the moisture content of heavy grade of paper having moisture weights of up to 90 grams per square meter.

29 Claims, 3 Drawing Sheets

APPARATUS AND METHODS EMPLOYING INFRARED ABSORPTION MEANS TO MEASURE THE MOISTURE CONTENT OF HEAVY GRADES OF PAPER

BACKGROUND OF THE INVENTION

1. Technical Field

The present invention relates to measuring the moisture content of heavy grades of paper (for purposes herein, paper having a fiber weight of at least 300 grams per square meter) during continuous manufacture. More particularly, the invention relates to apparatus and methods which can be used to effect such measurement by infrared absorption means.

2. Discussion of Related Art

The art of measuring the moisture (water) content of paper during its continuous manufacture by using the correspondence between the absorptance of particular infrared radiation wavelengths and the relative amounts of particular components present in the paper has been practiced for many years. Early approaches that were commercially successful are exemplified by U.S. Pat. No. 3,405,268 Brunton. Modified forms of these early approaches continue to be used.

In its simple form, the measurement is made by determining transmittances through the paper for two narrow bands of infrared radiation, one of which is very sensitive to absorption by water, (the moisture "absorption" or "measurement" band), and the other of which is relatively insensitive to absorption by water (the moisture "reference" band). The ratio of these transmittances is a function of water weight per unit area. The moisture measurement may be further refined by similarly measuring the cellulose fiber content of the paper and correcting the moisture measurement for scattering or absortion effects produced by the presence of fiber or other components. (See, e.g. U.S. Pat. Nos. 3,551,678 Mitchell and 4,577,104 Sturm.)

The successful use of infrared radiation for moisture measurement of paper has been limited to light or medium grades. In past efforts to address this limitation, it has been recognized that the limitation results from the very low penetrability of heavier grades by energy associated with conventional measurement and reference bands of both fiber and water. These problems are discussed in U.S. Pat. Nos. 3,793,524 Howarth and 3,551,678 Mitchell. The Mitchell patent suggests that the limitation can be "eased" by use of the O-H stretch region centered at about 1.45 microns in a case where a very high moisture content prevents transmission of measurable amounts of energy associated with the moisture absorption band. (Ordinarily, bands having wavelength centra of about 1.92 to about 1.96 microns are used for the moisture absorption band.). However, the use of a moisture absorption band centered at 1.45 microns is generally impractical because of the relatively high absorptances for both moisture and cellulose fiber at that wavelength. Furthermore, it appears that the primary problem in determining the transmittances of moisture absorption bands is not the inability to penetrate the paper with sufficient radiant energy, but rather the inability to produce precise determinations of these transmittances under conditions of varying temperature. This imprecision results from variations in the transmission spectrum for moisture with changes in temperature. Past methods aimed at compensating for this variation have employed thermistors or pyrometers. These attempts have not succeeded with heavy grades, possibly because they measure the surface temperature of the paper rather its average temperature throughout the entire thickness dimension.

Accordingly, contemporary approaches to measuring the moisture content of heavy grades of paper employ different means based on different physical phenomena. A favored approach has been to use microwave moisture gauging techniques. However, in addition to their considerable expense, these gauges perform poorly on paper which has a low fractional moisture content wherein bonding between water molecules and cellulose inhibits molecular rotation.

It has been discovered that very satisfactory measurements of the moisture content of heavy grades of paper can be made by infrared absorption means. It appears that these measurements, not being influenced by water/cellulose bonding, are superior to those produced by microwave moisture gauges.

An object of this invention is to provide apparatus and methods that enable measurement of the fractional moisture content, or percent moisture, of heavy grades of paper by infrared absoption means.

A further object of the invention is to provide apparatus and methods that overcome prior limitations to such measurement that arise from inadequate penetration through the paper by radiant energy associated with conventionally-employed fiber absorption bands.

Another object of the invention is to provide apparatus and methods for calculating the average temperature of a moving sheet of heavy-grade paper.

Another object of the invention is to provide apparatus and methods that produce accurate indications of the moisture weight per unit area of a sheet of paper, which when combined with conventionally-determined indications of basis weight or fiber weight, enable a measurement of the fractional moisture content of the paper.

Yet another object of the invention is to provide apparatus and methods as described which can be adapted to measure the moisture content of light or medium grades of paper.

SUMMARY OF THE INVENTION

In one aspect of the present invention, apparatus and methods that enable the measurement of fiber weight per unit area (Unless otherwise indicated, the word "weight" as used herein should be interpreted as "weight per unit area".) for heavy grades of paper having fiber weights of up to 1100 grams per square meter (hereinafter, "gsm") are provided. By that provision, these apparatus and methods enable measurement of the fractional moisture content, or percent moisture, of heavy grades of paper having moisture weights of up to 90 gsm, depending on the associated fiber weight. Infrared radiation is directed into a sheet of paper from a source located on one side of the sheet, and radiation corresponding to a plurality of selected narrow bands is detected on the other side of the sheet. One of these bands is designated a fiber absorption band and has a centrum selected from the range extending from 1.5 to 1.8 microns. A detector response associated with this band is combined with the detector response of an associated fiber reference band to produce a response to the fiber weight of the sheet. The fiber weight response is combined with a moisture weight response derived from the transmittances of a moisture absorption band and a moisture reference band, to yield a combined response from which a measurement of the fractional moisture content of the paper can be produced.

In another aspect, the invention provides apparatus and methods that overcome limitations related to the heightened temperature sensitivity which is encountered in measuring moisture weights for heavy grades of paper having moisture weights in excess of approximately 90 gsm. By this provision, these apparatus and methods enable the measurement of fractional moisture content, or percent moisture, for papers having fiber weights of up to 1100 gsm and moisture weights of up to 450 gsm. These limitations are overcome by using two moisture absorption bands and their associated reference bands to derive two responses to the moisture weight of the paper. As is further explained hereinafter, this permits calculation of the average temperature of the paper throughout its thickness dimension. (rather than its surface temperature). Once the average temperature is known, one of the moisture responses can be corrected for error related to the temperature of the paper to produce a corrected moisture response that is indicative of actual moisture weight. The corrected moisture response can then be combined with the fiber response to produce a combined response indicative of the moisture content of the paper.

Although the apparatus and methods herein described are primarily directed to the measurement of moisture content for heavy grades of paper, they employ means for changing the ratio of the intensity of radiation directed from the source to the intensity of radiation directed into the paper, thereby making the apparatus adaptable for measurement of lighter grades of paper.

DESCRIPTION OF THE PREFERRED EMBODIMENT

Figure 1:
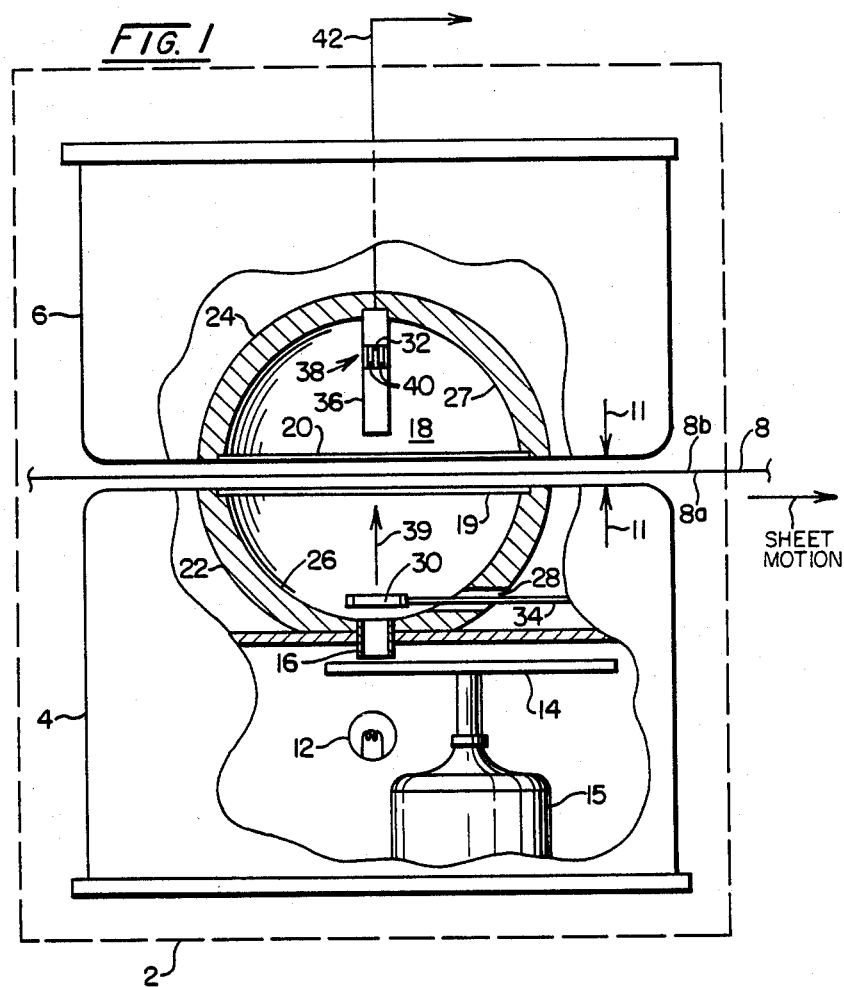
FIG. 1 is a partially schematic, partially sectional illustration of a sensor which may be used in accordance with the invention.
Figure 2:
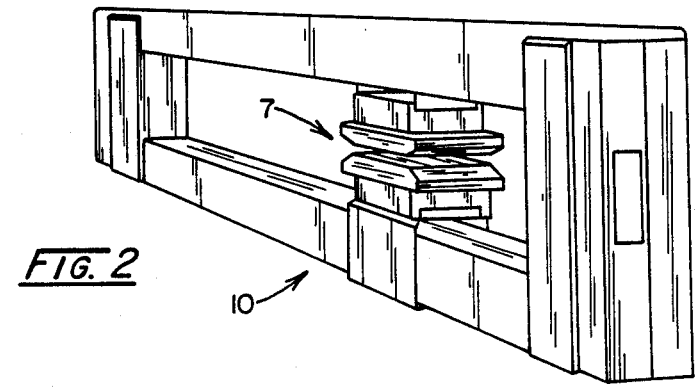
FIG. 2 is a perspective illustration of a sheet traversing structure on which a sensor incorporating the invention would typically be mounted when using the invention for the purpose herein described.

Referring to FIG. 1, the dashed line 2 designates a moisture sensor that comprises a first sensor head 4 (hereinafter, "source head") and a second sensor head 6 (hereinafter "detector head") that are typically contained within a head package 7 and are supported on opposite sides of a sheet 8 of paper by a conventional sheet traversing structure 10 (FIG. 2). The source and detector heads 4,6 are separated by a pass gap 11 of approximately 1.27 centimeters through which the sheet 8 passes. The sheet 8 is moving in the indicated direction during its continuous manufacture.

Although the invention can easily be incorporated in other sensor geometries, the embodiment herein described employs a dual-hemisphere geometry similar to those illustrated in U.S. Pat. Nos. 4,052,615 Cho and 4,027,161 Williams, et al.

The source head 4 contains a source 12 of infrared radiation connected to an external power supply (not shown) and positioned at approximately the focus of a parabolic reflector (not shown). The source head 4 additionally contains conventional cooling means for removing excess heat generated by the source 12. In an already-constructed prototype of the sensor 2, the source was a 200-watt quartz halogen lamp.

Installed in a conventional filter wheel 14 are separate optical filters (not shown). The filter wheel 14 is driven by a synchronous motor 15 and positioned so that the filters alternately pass through a radiation path which can be viewed as extending from the source 12 through a light pipe 16. Radiation passing through the filters and the light pipe 16 enters an approximately spherical cavity 18 and is directed through a transparent, circular plate 19 and into the sheet 8. In the prototype, the light pipe 16 had an inside diameter of approximately 2.22 centimeters.

The spherical cavity 18 is formed by a first hemispherical body 22 rigidly secured to and inside the source head 4 and a second hemispherical body 24 rigidly secured to and inside the detector head 6. The hemispherical bodies 22,24 have highly reflective, mirror-like surfaces 26,27, and an inside diameter of approximately 12.7 centimeters. The surfaces 26,27 are aligned and generally face opposite surfaces 8a and 8b of the sheet 8. The surfaces 26,27 are protected by transparent circular plates 19,20.

An entrance/exit slot 28 for a neutral density attenuator 30 was cut out from the first hemispherical body 22. The attenuator 30 was provided because the detector 32 would otherwise have been saturated in the absense of the sheet 8. The attenuator 30 was supported on one end of a generally L-shaped pivot arm 34 and positioned in the radiation path during standardization, but removed from the spherical cavity 18 during measurement. However, the attenuator 30 may serve the additional purpose of extending the linear range of the detector 32 so that the sensor 2 can be used for measuring lighter grades of paper wherein it is desired to direct radiation into the sheet at a lower intensity. In that application, the attenuator 30 would be positioned in the radiation path during both measurement and standardization modes. Positioning and removal of the attenuator 30 were effected via computer-controlled actuation of a solenoid (not shown) contained in the source head 4.

A portion of the second hemispherical body 24 corresponding to the thickness of a semicircular detector mounting plate 36 was cut out and the plate was rigidly secured therein. A detector assembly 38 was installed in the plate 36 at approximately the quasi-parabolic focal point of the surface 27. (Over a limited range centered at the transmission axis 39, the hemispherical surface 27 approximates a parabolic surface.). The detector assembly 38 was installed so that the photosensitive detector element 32 (A high-detectivity lead sulfide photoresistive detector was used.) could receive radiant energy from both sides of the plate 36. To this end, a central bore (not shown) axially aligned with the focal point provided a window on one side of the plate 36. The detector element 32 was sandwiched between two blocking filters 40 that were provided to prevent ambient light from reaching the element. The element 32 and the blocking filters were circular and of a slightly larger diameter than the central bore, and were disposed within a counterbore (not shown) which was slightly larger than, and coaxial with, the central bore. They were locked in place by an access plate (not shown) which was fitted to a milled-out portion of the side of the plate 36 opposite that of the central bore, and was secured thereto. A hole having the same diameter and axis as the central bore was drilled through the access plate, thus providing a second window so that the detector element 32 could receive radiation from both sides of the plate 36. Leads from the detector element 32 extended through a small hole (not shown) drilled from the edge of the plate 36 to the counterbore.

The filters installed in the filter wheel 14 were initially selected to pass radiation in narrow bandwidths centered at about 1.56, 1.79, and 1.958 microns. The word "narrow" as applied to the word "bands" or "bandwidths" herein is intended only to convey the reality that currently available optical filters pass a narrow bandwidth at a given wavelength centrum, even though one might desire to use only the wavelength corresponding to the centrum. The above-specified narrow bands corresponded to fiber absorption, fiber and moisture reference, and moisture absorption wavelengths, respectively.

It will be recognized that after employing conventional standardization and calibration procedures, individual detector responses 42 indicative of the transmittances of these narrow bands through the sheet 8 are produced from the detector 32. The detector responses 42 were initially processed similarly to the system described in U.S. Pat. No. 4,577,104. However, certain changes related to compensating for error resulting from changes in sheet temperature were made to that system, as will be further described hereinafter.

Figure 4:
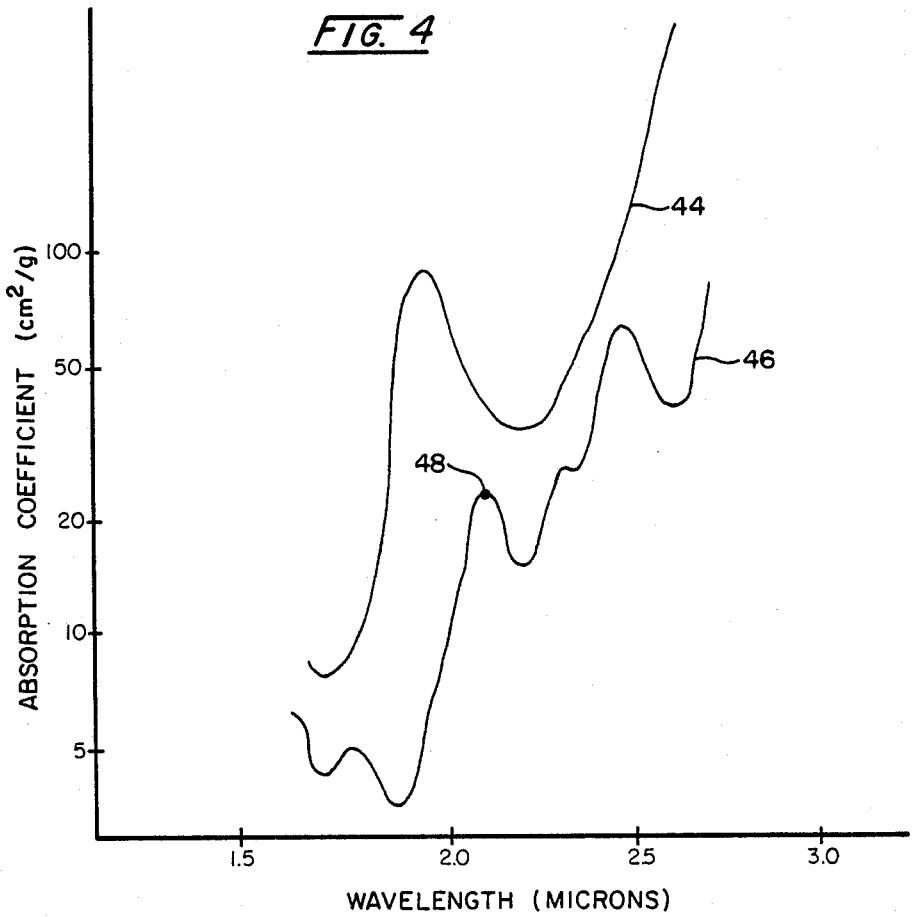
FIG. 4 is a logarithmic plot of the absorption spectra for water and cellulose in that portion of the infrared region extending from about 1.6 to about 2.7 microns.

Referring to FIG. 4, numerals 44 and 46 designate infrared absorption curves for water and cellulose fiber, respectively. Because of the strength of the absorption band for fiber that is centered at about 2.12 microns (point 48 on curve 46) as compared to the relatively weak absorption by water in that region, it has been favored in prior infrared moisture gauging apparatus which determine the transmittance of fiber-sensitive wavelengths in order to correct an indicated transmittance of moisture-sensitive wavelengths. (See, e.g., U.S. Pat. Nos. 3,551,678 and 4,577,104.). However, it is primarily the strength of that absorption band that makes these apparatus unsuitable for measuring the moisture content of heavy grades of paper. For heavier grades of paper and at practicable source intensities, substantially all radiant energy associated with this band is absorbed, leaving too little energy to derive an indication of fiber weight and, consequently, no indication of fiber weight with which to compensate an indication of moisture weight.

Rather than resorting to microwave or radio frequency gauging techniques, I elected to work with the wavelength range extending from about 1.5 to about 1.8 microns (see FIG. 4), and to select therefrom two narrow bands. One of these, designated a fiber absorption band was centered at about 1.56 microns. The other, designated a fiber reference band was centered at about 1.79 microns. It is stressed that other combinations of narrow bands selected from this range can be used to advantage in accordance with this invention. Moreover, the fiber reference band can be selected from area outside this range while maintaining the advantages hereby provided, though with less facility in compensating the indication of fiber weight for cross-effects of absorption by water in the fiber absorption and reference bands. Accordingly, it is preferable to select both the fiber absorption and reference bands from within this range, to select these bands from comparatively flat portions of the fiber absorptance curve, and to make such a selection that provides maximal difference in fiber absorption coefficients while providing minimal difference in water absortion coefficients.

Figure 5:
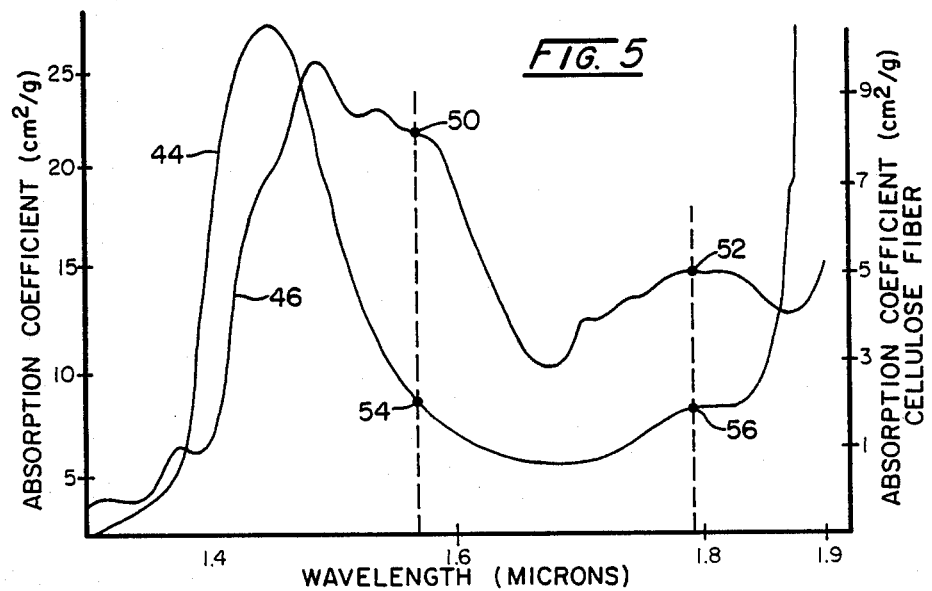
FIG. 5 is a graph showing the absorption spectra for water and cellulose in the range extending from about 1.3 to about 1.9 microns.

Thus, referring to FIG. 5, the numerals 50 and 52 designate the fiber absorption and reference wavelengths of 1.56 and 1.79 microns chosen for the prototype. The corresponding points 54,56 on the moisture absorption curve 44 had substantially the same moisture absorption coefficients. I used a moisture absorption band centered at about 1.958 microns and an associated moisture reference band centered at about 1.79 microns. The coincidence of the fiber and moisture reference bands is unnecessary. However, by selecting these to coincide one can minimize the number of bands required and facilitate application of the invention to existing sensor designs.

In selecting the fiber absorption and reference bands, there may be some difference in their moisture absorption coefficients, and the effective use of known calibration schemes can correct error associated with this difference. However, as the difference becomes larger, it becomes more difficult to correct this error, and at differences exceeding about twelve centimeters squared per gram the inability to distinguish absorption due to fiber from that due to water renders such correction impracticable.

I have found that when the limiting factor in the ability to make an acceptable moisture measurement is high fiber weight (generally, when the fiber weight exceeds 300 gsm, I can overcome the limitation by using a ratio of the transmittances of fiber absorption and fiber reference bands taken from the above-described range to correct a ratio of the transmittances of moisture absorption and moisture reference bands which are typically used. By this approach, I have produced accurate measurements of moisture content for papers having fiber weights of up to 1100 gsm with moisture weights of up to 80 gsm. The results are surprising, since it appears that the absorption curves associated with the O-H stretch overtones of fiber and water in the range extending from about 1.45 to about 1.65 microns are similar in shape, and would render a measurement of either component unacceptable. Moreover, the relatively small differences in fiber absorption coefficients in the range extending from about 1.5 to about 1.85 microns do not make that range particularly attractive for fiber measurement. However, these overtones are slightly shifted in relation to each other, (due, apparently, to differences in the geometries of the O-H bonds for water and cellulose), and this slight shift permits use of the range extending from about 1.5 to about 1.8 microns for providing an indication of fiber weight that is substantially independent on moisture content. Even though differences in fiber absorption coefficients for fiber absorption and fiber reference bands selected from this range are relatively small, the differences are more pronounced in heavier grades where increased internal scattering increases the effective path length of photons. This difference is sufficient to enable accurate measurement of fiber weight for papers having fiber weights ranging from 90 to 1100 gsm.

Figure 6:
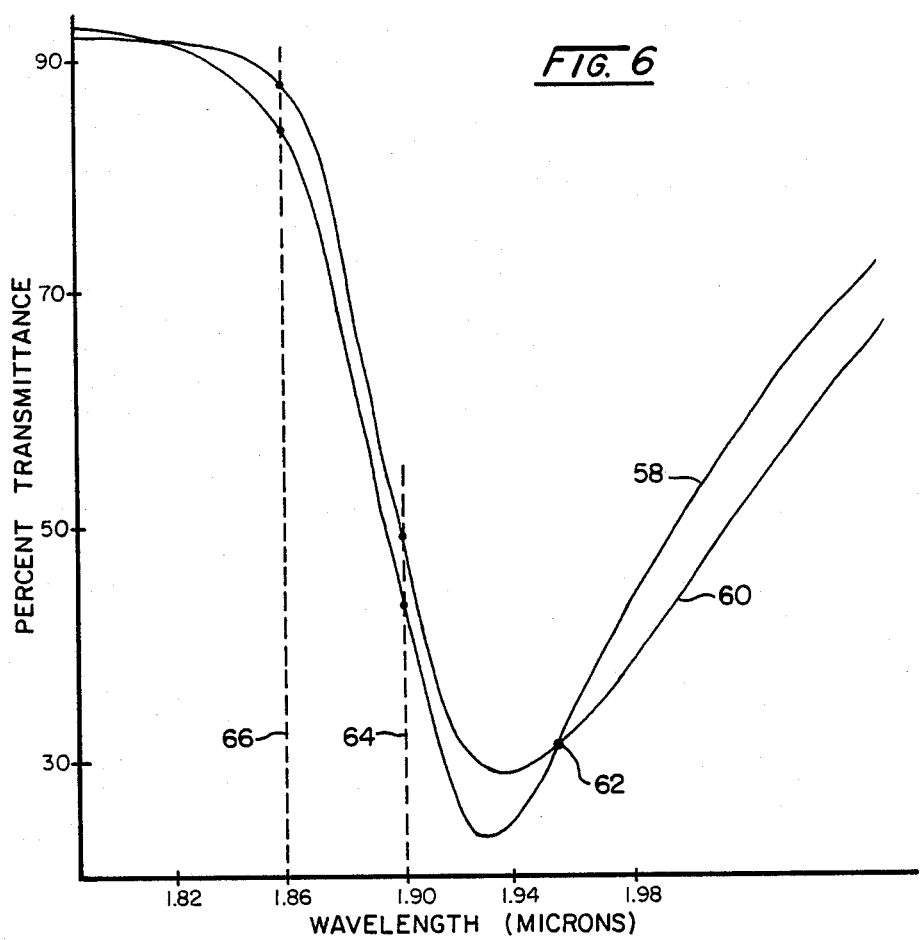
FIG. 6 is a graph illustrating the change in the transmission spectrum for water in response to a change in temperature.

Although the ability to overcome the limitation imposed by high fiber weight enables measurement of moisture content for some heavy-grade papers, one is still faced with the problem of temperature sensitivity for paper which has a relatively high moisture weight. This problem can be explained with reference to FIG. 6 which shows the transmission spectrum for 100 gsm water at 27 degrees celsius (curve 58) and at 89 degrees celsius (curve 60). From FIG. 6, it can be seen that over substantially the entire range of wavelengths from which moisture absorption bands are typically selected, the shape of the transmission spectrum (and therefore the absorption spectrum) is altered by changes in temperature. At higher moisture weights, there is a significant "reshaping" of the moisture absorption band as seen by the detector 32 because the band, though narrow, does have some bandwidth. That is, the distribution of radiant energy within the band is much different on the detector side of the sheet 8 from what it was on the source side. This reshaping effectively amplifies the error associated with temperature-related changes in the moisture absorption coefficient, so that at higher moisturer weights the moisture measurement is extremely temperature-sensitive.

The curves 58,60 intersect at 1.958 microns (point 62) where the absorption coefficient for water is the same for the two indicated temperatures. One can minimize the effect of sheet temperature sensitivity by selecting this wavelength as the centrum of the moisture absorption band. However, this puts a limit on the range of moisture weight that can be measured because of the low transmittance at that wavelength. To overcome this problem, I changed the filter for the moisture absoption band to provide a centrum of 1.90 microns (point 64) instead of the original 1.958 microns. This had the desirable effect of increasing the energy transmitted through the sheet 8. As suggested above, the adverse effect of this change is that the absorption coefficient at 1.90 microns changes significantly with changes in temperature. I corrected for this effect, as further explained below, by adding to the filter wheel 14 a filter that passed a narrow band centered at 1.86 microns (point 66), thus providing a second moisture absorption band.

It can be seen from the graph that the temperature sensitivity at 1.86 microns is greater than at 1.90 microns, and that for both of these wavelengths the moisture absorption coefficient varies significantly with temperature. In effect, I used the second moisture absorption band and an associated reference band to measure the amount of shift in the water absorption spectrum in order to calculate the average temperature of the sheet 8. This enabled me to apply a correction to the transmittance, as indicated by the first moisture absorption and reference bands, so that the final indication of moisture weight was unaffected by the temperature of the sheet 8. The 1.79 micron band was used as a reference band for both moisture absorption bands. The approach is more fully described below.

Assuming purely exponential absorption one can determine a first moisture ratio, G1, as the ratio of the transmittance of the first moisture reference band to the transmittance of its associated absorption band. If the fiber absorption coefficients are equal for the two bands, the effect of absorption by fiber will cancel. Otherwise this effect can be accounted for by a conventional calibration function. By measuring G1 at a first average temperature, T1, and using a form of the Beer-Lambert Law, one can determine an effective absorption coefficient for moisture that is attributable to the first moisture absorption band at that temperature:

$$m1 = ln(G1)/W, \text{ or} \quad (1)$$

$$W = ln(G1)/m1, \quad (2)$$

where "m1" is the effective moisture absorption coefficient of the first moisture absorption band, and "W" is the moisture weight per unit area.

Similarly, one can determine at the same temperature a second moisture ratio, G2, as the transmittance of the second moisture reference band to the transmittance of its associated absorption band, and determine an effective moisture absorption coefficient attributable to the second moisture absorption band:

$$m2 = ln(G2)/W, \text{ or} \quad (3)$$

$$W = ln(G2)/m2. \quad (4)$$

In like fashion, the effective moisture absorption coefficients, m1 and m2, are determined for several different temperatures to yield two sets of data which can be used to describe each effective moisture absorption coefficient as a function of temperature. Although the functions are not quite linear, they can be expressed as linear functions over a limited range of temperatures. I have experimentally determined that this expression is quite adequate for use over temperature ranges typically encountered in paper manufacturing. The functions can be expressed, for example, as follows:

$$m1 = a*T + b \quad (5)$$

$$m2 = c*T + d, \quad (6)$$

where "a,c" and "b,d" are the slopes and intercepts, respectively, of the linearized functions as determined during laboratory calibration.

Substituting the "m1" and "m2" expressions of equations 5 and 6 into equations 2 and 4 and solving for "T" yields the following:

$$T = \frac{b * ln(G2) - d * ln(G1)}{c * ln(G1) - a * ln(G2)}. \quad (7)$$

When "G1" and "G2" are measured on-line, the calcuated value of temperature, T, can be inserted in equation 5 to determine a corrected effective moisture absorption coefficient associated with the first moisture absorption band. The corrected effective moisture absorption coefficient can then be substituted for "m1" in equation 2 to calculate the true moisture weight of the sheet 8.

The true moisture weight can then be combined with a basis weight measurement derived from any conventional means such as a beta gauge, for example, or with a fiber weight measurement to produce a measurement of the fractional moisture content or percent moisture of the sheet 8. However, it will be recognized that it is far more economical to provide both necessary measurements in an integral structure such as apparatus disclosed herein.

Figure 3:
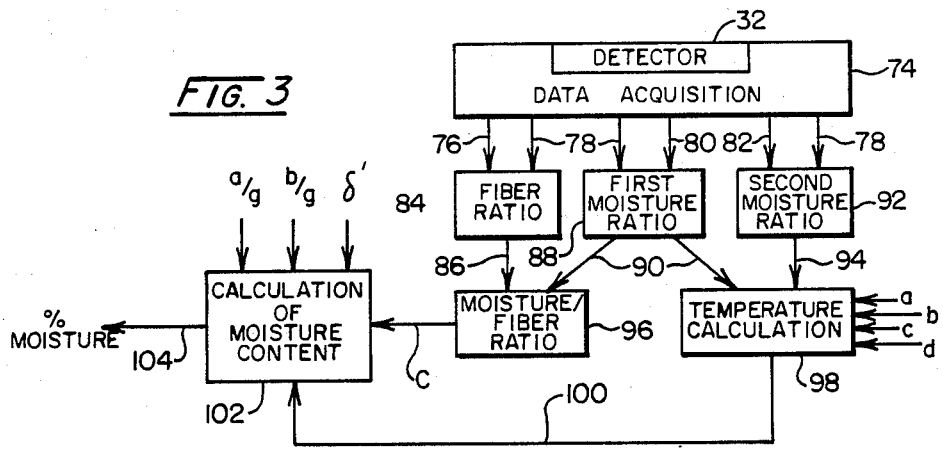
FIG. 3 is a flow diagram illustrating a preferred information handling procedure for processing detector responses indicative of the transmittances of narrow bands of radiation selected for practicing particular aspects of the invention.

Reference is now made to FIG. 3 which illustrates the preferred information handling procedure in processing the detector responses 42. The photosensitive element 32 is part of a data acquisition system 74 which may be similar to apparatus described in U.S. Pat. No. 4,300,049 Sturm. The system 74 produces responses 76,78,80,82 indicative of the transmittances of detected radiation in the narrow bands centered at 1.56, 1.79, 1.90, and 1.86 microns, respectively. The transmittance values indicated by the responses 76,78,80,82 are typically provided in the form of electrical signals which are digitized and then processed by a digital computer.

A function of the ratio of transmittances of the fiber absorption and fiber reference bands is formed at 84 to produce a fiber response 86 to the fiber contained in the sheet 8. The function of the first moisure ratio, G1, is formed at 88 to produce a first moisture response 90 to the moisture contained in the sheet 8. A function of the second moisture ratio, G2, is formed at 92 to produce a second moisture response 94 to the moisture contained in the sheet 8.

The fiber, first moisture, and second moisture responses 86,90,94 may be represented as "ln(R/A)", where "R" is the transmittance of the applicable reference band and "A" is the transmittance of the applicable absorption band. The fiber response 86 is indicative of the fiber weight of the sheet 8 and can be expressed as follows:

$$ln(R/A) = g^*(F + \delta W)^* f(F), \quad (8)$$

where "F" is the fiber weight per unit area of the sheet 8, "$\delta W$" is a second error function to account for differences, if any, in the moisture absorption coefficients of the fiber absorption and fiber reference bands, "g" is a constant determined in calibration, and "f(F)" is a first error function dependent on the scattering characteristics and broadband absorber content of the fiber component of the sheet. The first moisture response 90 is indicative of the moisture content of the sheet 8 and can be expressed as follows:

$$ln(R/A) = m1^* W^* f(F), \quad (9)$$

where "W" is the moisture weight per unit area of the sheet 8, and "m1" is the effective moisture absorption coefficient for the first moisture absorption band.

A function of the ratio of the first moisture response 90 and the fiber response 86 is formed at 96 to produce a combined response "C" that is substantially independent on the error function "f(F)" but is dependent on the second error function "$\delta W$". Thus, the combined response C can be expressed as follows:

$$C = \frac{(m1)W}{g(F + \delta W)}. \quad (10)$$

The basis weight, or total weight per unit area of the sheet 8 is substantially equal to the combined weights of fiber and moisture (F+W). Thus expression "10" may be alternatively expressed as follows:

$$C = (ml/g) * \frac{W/(F + W)}{[F/(F + W)] + \delta * [W/(F + W)]}, \quad (11)$$

and expression "11" may in turn be expressed as:

$$C = (ml/g) * \frac{\%W}{\%F + \delta * \%W}, \quad (12)$$

where "%F" is the percent fiber in the sheet 8 and "%W" is the percent water or moisture in the sheet.

Since $\%F = 1 - \%W$, expression "12" may also be expressed as follows:

$$(ml/g) * \frac{\%W}{(1 - \%W + \delta * \%W)} = (ml/g) * \frac{\%W}{1 + \%W(\delta - 1)}. \quad (13)$$

$$\text{Letting } \delta - 1 = \delta', \%W = \frac{C(g/ml)}{1 - \delta'* C *(g/ml)}. \quad (14)$$

As explained above, at high moisture weights "m1" must be considered a function of temperature. From equation 5, $m1 = a^*T + b$. Thus, equation 14 may be expressed as follows:

$$\%W = \frac{C(1/[(a/g) * T + (b/g)])}{1 - \delta' * C * (1/[(a/g) * T + (b/g)])}. \quad (15)$$

The first moisture response 90 is also an input, as is the second moisture response 94, to a temperature calculating function 98. The temperature calculating function 98 employs the responses 90,94 and data derived during a calibration procedure, such as that described above, to calculate the average temperature of the sheet 8. The temperature is communicated via response 100 to final operation 102 which utilizes response C, response 100 and calibration data a/g, and b/g to produce a measurement response 104 that is calibrated in accordance with the second error function $\delta W$. The measurement response 104 is indicative of the fractional moisture content or percent moisture of the paper sheet 8, and is substantially independent of variations in temperature, scattering characteristics, and broadband absorber content.

When the temperature calculation aspect of the invention is not employed (generally, when moisture weight is under about 90 gsm), the information handling procedure may be substantially the same as that described in U.S. Pat. No. 4,577,104.

Those skilled in the art will recognize that numerous calibration schemes may be designed which are different from, but functionally equivalent to, that described above once the advantages associated with measuring the sheet temperature via the use of two moisture absorption bands are realized. It is also apparent that accounting for the fiber weight of the paper by infrared absorption means is unnecessary for practicing this aspect of the invention, since an output of a separate apparatus (such as a conventional beta gauge, for example) that determines total weight per unit area may be combined with the output of an infrared-based moisture gauge which produces an output indicative of moisture weight and which accounts for the average temperature of the sheet 8 in accordance with the teaching of this aspect.

Similarly, it will be recognized that when fiber weight is determined by infrared absorption means, fiber absorption bands selected from the range extending from 1.5 to 1.8 microns, but different from that particularly selected for purposes of development and description herein may be used without departing from the spirit and scope of that aspect of the invention.

Accordingly, the above description is illustrative in purpose and is not intended to restrict the scope of the invention beyond that defined by the following claims and their equivalents.

What is claimed is:

1. Apparatus for use in measuring the moisture content of paper during its continuous manufacture, comprising:
    (a) a source of infrared radiation positioned on one side of the paper for directing infrared radiation into the paper;
    (b) means, including at least one detector positioned on the opposite side of the paper from the source, for individually detecting a plurality of selected bands of infrared radiation emitted from the source and transmitted through the paper, the plurality including three narrow bands corresponding to a fiber absorption band, a moisture absorption band, and a reference band, wherein the centrum of the fiber absorption band is in a range extending from 1.5 microns to 1.8 microns, the apparatus being adapted to produce detector responses that can be processed to produce a measurement of the fractional moisture content or moisture percentage of the paper, and the response being indicative of the transmittances of the selected bands.

2. Apparatus as in claim 1 further comprising means for processing the detector responses to produce the measurement.

3. Apparatus as in claim 2 wherein the processing means is adapted to form a ratio of the transmittances of the fiber absorption band and a fiber reference band to produce a fiber response to the fiber content of the paper, the measurement being determined in part by the fiber response.

4. Apparatus as in claim 3 wherein the centrum of the fiber reference band is in a range extending from 1.5 to 1.8 microns.

5. Apparatus as in claim 4 wherein the the moisture absorption coefficients for the fiber absorption and fiber reference bands differ, if at all, by not more than twelve centimeters squared per gram.

6. Apparatus as in claim 5 wherein the processing means is adapted to form a first moisture ratio of the transmittances of the moisture absorption band and a moisture reference band to produce a first moisture response to the moisture content of the paper, the measurement being determined in part by both the fiber response and first moisture response.

7. Apparatus as in claim 6 further comprising means for changing the ratio of the intensity of radiation emitted from the source to the intensity of radiation directed into the sheet.

8. Apparatus for use in measuring the moisture content of a sheet of paper during its continuous manufacture via first measuring the transmittances through the sheet of a plurality of selected narrow bands of infrared radiation, comprising:
    (a) a first sensor head positioned on one side of the sheet and containing a source of infrared radiation;
    (b) a second sensor head positioned on the opposite side of the sheet from the first sensor head, the sensor heads being separated by a pass gap through which the sheet passes;
    (c) means for supporting the sensor heads on opposite sides of the sheet;
    (d) a first body rigidly secured to the first sensor head, the first body having a highly reflective surface generally facing a surface of the sheet corresponding to the one side;
    (e) a second body rigidly secured to the second sensor head, the second body having a highly reflective surface substantially aligned with the highly reflective surface of the first body and generally facing the opposite surface of the sheet;
    (f) means for directing into the sheet the infrared radiation emitted from the source; and
    (g) means, including at least one detector contained within the second sensor head and positioned to detect radiation reflected from the reflective surfaces, for individually detecting the selected narrow bands of infrared radiation wherein the selected narrow bands include three bands corresponding to a fiber absorption band having a centrum in the range extending from 1.5 to 1.8 microns, a fiber reference band, and a moisture absorption band, the detecting means being adapted to individually produce detector responses for each of the three narrow bands.

9. Apparatus as in claim 8 wherein the water absorption coefficients of the fiber absorption and fiber reference bands differ, if at all, by not more that twelve centimeters squared per gram.

10. Apparatus as in claim 9 wherein the centrum of the fiber reference band is in a range extending from 1.5 to 1.8 microns.

11. Apparatus as in claim 10 further comprising means in communication with the detecting means for processing the detector responses to produce a measurement of the moisture content of the sheet.

12. Apparatus as in claim 11 wherein the measurement is determined at least in part by two ratios, one being a ratio of the transmittances of the fiber absorption band and the fiber reference band, and the second being a ratio of the transmittances of the moisture absorption band and a moisture reference band.

13. A method for measuring the moisture content of paper during continuous manufacture thereof, comprising the steps of:
    (a) directing infrared radiation into the paper;
    (b) individually detecting the radiation transmitted through the paper for each of a plurality of selected narrow bands including a fiber absorption band having a wavelength centrum selected from a range extending from 1.5 to 1.8 microns, a moisture absorption band, and at least one reference band, to produce detector responses indicative of the transmittances of the selected bands; and
    (c) processing the detector responses to produce a measurement of the moisture content of the paper.

14. A method as in claim 13 wherein the processing step comprises forming two ratios to produce two responses, one to the fiber weight per unit area of the paper and the other to the moisture weight per unit area of the paper, the ratio associated with the one response being a ratio of the transmittances of the fiber absorption band and a fiber reference band, and the ratio associated with the other response being a ratio of the transmittances of the moisture absorption band and a moisture reference band.

15. A method as in claim 14 wherein the fiber reference band is selected from the range extending from 1.5 to 1.8 microns.

16. A method as in claim 15 wherein the processing step further comprises forming a function of the ratio of the two responses to produce a combined response that is substantially independent of fiber scattering characteristics and broadband absorber content of the paper.

17. In a method for measuring the moisture content of a sheet of heavy-grade paper during its continuous manufacture, the steps comprising:
   (a) determining the transmittances of a first moisture absorption band and an associated moisture reference band to produce a first moisture response to the moisture contained in the sheet;
   (b) determining the transmittances of a second moisture absorption band and an associated reference band to produce a second moisture response to the moisture contained in the sheet;
   (c) calculating the average temperature of the sheet by means including the first and second moisture responses to produce a calculated average temperature.

18. In a method as in claim 17, the further step comprising correcting the first moisture response in accordance with the calculated average temperature to produce a corrected first moisture response.

19. In a method as in claim 18, the further step comprising measuring either the total weight per unit area or the fiber weight per unit area of the sheet and combining the measurement with the corrected first moisture response to produce a measurement of the fractional moisture content or percent moisture of the sheet.

20. Apparatus comprising:
   (a) means for determining the transmittances through a moving sheet of paper of a plurality of narrow bands of infrared radiation, the plurality including a first moisture absorption band sensitive to absorption by moisture contained in the sheet, a reference band associated with the first moisture absorption band but being less sensitive to absorption by the moisture, a second moisture absorption band sensitive to absorption by moisture contained in the sheet and a reference band associated with the second moisture absorption band but being less sensitive to absorption by the moisture; and
   (b) means employing indications of the transmittances for calculating the average temperature of the sheet.

21. Apparatus as in claim 20 wherein the moisture weight of the sheet exceeds ninety grams per square meter.

22. Apparatus as in claim 21 further comprising means for producing an indication of the moisture weight per unit area of the sheet, which moisture weight indication is substantially independent on variations in the average temperature.

23. Apparatus as in claim 22 further comprising means for producing an indication of the fiber weight per unit area of the sheet.

24. Apparatus as in claim 23 wherein the means for producing an indication of the fiber weight employs a source of infrared radiation positioned on one side of the sheet to direct radiation into the sheet, at least one detecting element positioned on the opposite side of the sheet, and two filters selected to pass fiber absorption and fiber reference bands of infrared radiation to the detecting element.

25. Apparatus as in claim 24 wherein the centrum of the fiber absorption band is selected from the range extending from about 1.5 to about 1.8 microns.

26. Apparatus as in claim 25 wherein the centra of both the fiber absorption and fiber reference bands are selected from the range extending from about 1.5 to about 1.8 microns.

27. Apparatus as in claim 26 wherein the indication of fiber weight is combined with the indication of moisture weight to produce an indication of the fractional moisture content of the sheet.

28. Apparatus as in claim 27 wherein the moisture absorption coefficients of the fiber absorption and fiber reference bands differ, if at all, by not more than twelve centimers squared per gram.

29. Apparatus as in claim 28 further comprising means for changing a ratio of the intensity of infrared radiation emitted from the source to the intensity of infrared radiation directed into the sheet.

* * * * *